US00PP09154P

United States Patent [19]

Roberson

[11] Patent Number: Plant 9,154

[45] Date of Patent: Jun. 6, 1995

[54] CANNA PLANT 'BUGLE BOY'

[76] Inventor: Robert J. Roberson, 31706 E. Pink Hill Rd., Grain Valley, Jackson County, Mo. 64029

[21] Appl. No.: 226,211

[22] Filed: Apr. 11, 1994

[51] Int. Cl.[6] ..... A01H 5/00
[52] U.S. Cl. ..... Plt./68.1
[58] Field of Search ..... Plt. 68.1

*Primary Examiner*—James R. Feyrer

[57] ABSTRACT

A new and distinct cultivar of Canna, substantially as described and illustrated herein, characterized particularly as to novelty by its dwarf height, with overall compact characteristics, a multiplication rate of six to twenty plants per growing season, an influorescence with a unique distribution of bright red-orange and yellow colors, and strong winter storage capability providing a cultivar well suited as a garden or pot plant having no unusual susceptibility to the traditional Canna diseases and insects.

1 Drawing Sheet

SUMMARY OF THE INVENTION

This invention relates to a new and distinct Canna cultivar which is outstanding because of its dwarf height, with overall compact growth characteristics, a multiplication rate of six to twenty plants per growing season, a combination of bright red-orange and yellow flowers, a strong winter storage capability and primarily selected for those characteristics. This selection was made from a specially designed Canna hybridizing program with said hybird cultivars being planted and grown in Grain Valley, Mo.

ORIGIN AND ASEXUAL REPRODUCTION

Asexual reproduction of this cultivar by dividing the rhizome was directed by me, such reproduction establishing that the plant does in fact maintain the characteristics described, in successive generations.

It should be noted that the plant was initially selected from a Cannas planting being grown near Grain Valley, Mo. in a cultivated area and has since been reproduced by dividing the rhizome in the vicinity of Grain Valley, Mo. with the new and distinct characteristics stated herein, found to be maintained through successive generations as before recited.

*Canna*×*generalis* is a group of tropical to sub-tropical herbaceous plants grown primarily for their rapid growth and vivid, flamboyant, summer blooms. They are grown in USDA zones9–10 as a perennial and in USDA zones 3–8 as an annual. General growth habit includes an erect central (main) stalk with large tropical alternate leaves. This massive (24"–96") plant is topped by a colorful, inflourescent display. They are of easy cultivation in any fertile, moist soil, especially soils high in humus.

The cultivar of Liberty ® Bugle Boy may further be described as having a number of distinctive characteristics which are enumerated in the succeeding specific description but broadly stated as comprising a dwarf height (52 cm–66 cm), with overall compact growth characteristics and a multiplication rate of six to ten plants in zone 5 and as high as 20 in zone 9 per growing season. The floral dislay is a combination of bright red-orange and yellow flowers. The bloom period begins at approximately twelve (12) weeks after planting and continues until frost.

I have chosen to identify this new cultivar as Canna 'Bugle Boy'. This cultivar is being marketed under Liberty ® Bugle Boy.

BRIEF DESCRIPTION OF THE DRAWING

The accompanying photograph shows as nearly true as it is reasonably possible to make the same, in a color illustration of this character, typical flowers of the new variety. The photographic drawing illustrates the flower from and the novel and distinctive combination of bright red-orange and yellow flowers.

In the photograph.

DETAILED DESCRIPTION

Figure 1:
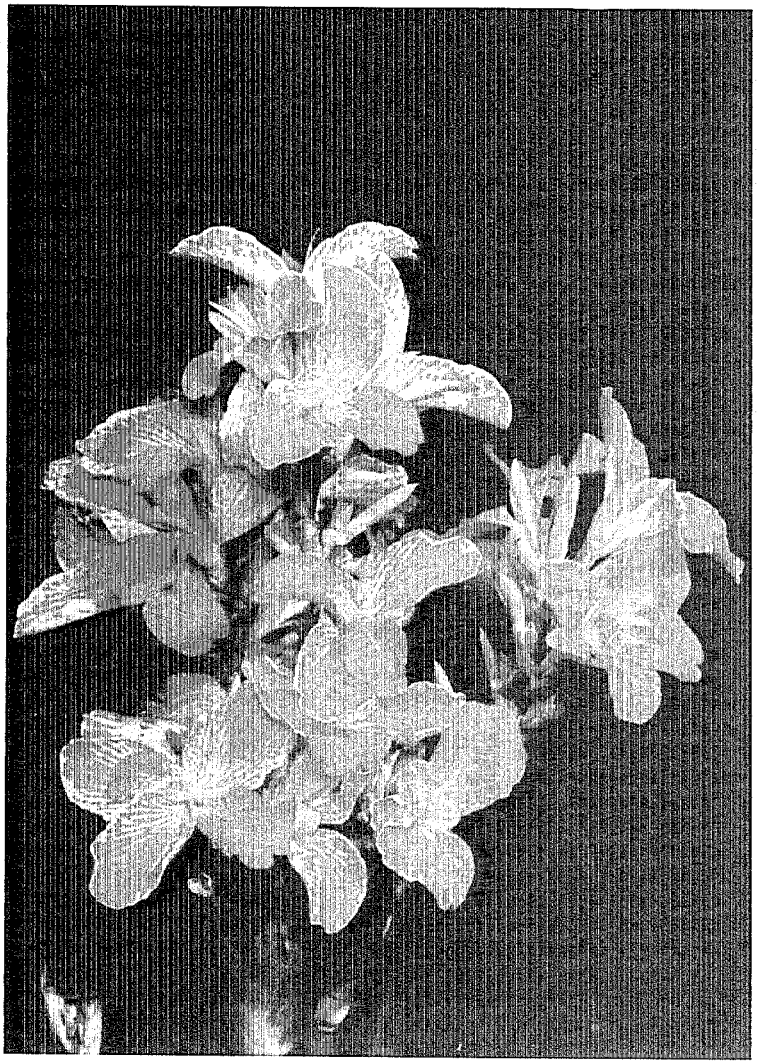
FIG. 1 illustrates the mature flower.

In order to more specifically identify the cultivar, descriptive details are set forth hereinafter, along with related aspects of the plant which serve to distinguish the same, all colors being noted as compared with the Pantone Matching System (PMS). The measurements and colors were recorded form mature plants grown in the vicinity of Grain Valley, Mo., unless stated otherwise.

Parentage:

*Seed parent.*—Canna 'Ambrosia'.

*Pollen parent.*—Canna 'Circus Clown'.

Propagation: Asexual reproduction by rhizome division started near Grain Valley, Mo.

Plant descriptions:

*Influorescence and reproductive parts.*—The overall influorescence is thursoid (mixed) and is approximately 27 cm in length by 17 cm in width when mature. The terminal axis is indeterminate and the lateral axes are cymose and determinate. The large, zygomorphic, hermaphrodite flowers are borne terminally and more or less erect in a racemose influorescence and are at anthesis together with one that is in bud. The flowers, borne on short pedicels occur in pairs forming a two-flowered cincinnus. Each flower is subtended by a bract. The outer whorl of the perianth consists of three free, imbricate sepals, the inner whorl of three basically united petals. There are typically three to five petaloid staminodes (showy portion of influorescence) with the smaller fertile petaloid stamen and style visible at the center of the flower. Colors of "Petals" (showy portion composed of petaloid staminodes): PMS #186 (Red) and PMS #107 (Yellow), both occurring in random splashes. The perianth segments (petals and sepals) are also PMS #186 (Red) and PMS #107 (Yellow), both occurring in random splashes, but are a reduced pigment intensity and have a glaucous (powdery) coating (grey-white).

Due to the unusual composition of the reproductive parts, self pollination is more common in cannas than is cross pollination. The petaloid stamen and style are visible at the center of the flower. The stamen can be recognized by the presence of the single anther-cell along its upper margin. The pistil is made up of the stigma or tip, the petaloid style and a three locular ovary. The ovary is borne on a short pedicel and each loculus contains numerous anatropous ovule attached to an axile placenta. The capsule has a warty pericarp that distintegrates at maturity to release the seeds.

*Terminal axis.*—Indeterminate.

*Lateral axis.*—Cymose and determinate.

*Petaloid staminodes.*—PMS No. 186 (Red) and PMS No. 107 (Yellow) occurring in random splashes.

*Perianth segments.*—PMS No. 186 (Red) and PMS No. 107 (Yellow) with a reduced pigment intensity and have a glaucous (powdery) coating (grey-white).

Bud: Bud size is 5 cm to 7 cm comprised of:

*Sepal.*—0.7 cm to 1.2 cm.

*Petal.*—2 cm to 3 cm.

*Emerging stamenodes.*—Varying from 1.5 cm to 4 cm.

Color of reproductive parts:

*Anther.*—Dark Brown (PMS No. 476 ) to black at dehiscence.

*Stigma.*—Translucent cream to white.

*Ovary.*—Medium Green.

*Stamen.*—Blend of red/orange to yellow.

*Style.*—Blend of red/orange to yellow with splashes and freckles.

*Seeds.*—At maturity are oval, near black and approximately 4 mm by 7 mm in size.

Leaves: The alternate leaves are long ovate in shape and have pinnate veins and a dominate mid-rib. They are large, broad, simple, and entire with sheathing petioles. The average size of leaves at maturity is 50 cm in length by 26 cm in width. The dominate color in young leaves is PMS No. 377 and in mature leaves is PMS No. 371.

*Tubers (rhizomes).*—These tuberous rhizomes are a cream-white in color and are covered by "papery" scale-like leaves arising at the nodes. This paper-like layering is brown (PMS No. 439) with darker brown (PMS No. 440) veining. The average rhizome is 10 cm in length and 2.5 cm in width.

*Roots.*—The fleshy roots arise from the internodes of the rhizomes and vary from 1–3 mm in diameter and are an average length of 29.5 cm.

*Flowering time.*—The bloom period begins at approximately twelve (12) weeks after planting (when planted at the recommended season and given reasonable care) and continues until frost. No pruning or pinching is required for optimum flowering performance. Spent blooms are shed quickly (approximately 36 hours after opening).

*Diseases.*—No unusual susceptibility to diseases noted to date.

*Insects.*—No unusual susceptibility to insects noted to date.

*General observations.*—"Bugle Boy" Canna, with its dwarf and very compact growth habit is ideal for the smaller garden and landscape designs and the patio/pot culture trend. The bicolor splashes of bold red/orange and yellow are strongly contrasting and very striking in the landscape.

For the purpose of ornamental horticulture in our present living environments which include smaller yards and patio gardening, Liberty® Bugle Boy is ideal due to several characteristics. These plant characteristics are:

Unique Influorescence: The uniqueness of this cultivar color influorescence lies in the extreme variation from 90% red to 10% yellow, phasing through 50% red—50% yellow all the way to 90% yellow to 10% red. While some other cannas, including Circus Clown do show some (approximately 20%) variation in color combined in the influorescence, none do so to the extent of Liberty® Bugle Boy. The bicolor splashes of bold red/orange and yellow are strongly contrasting and very striking in the landscape. Marketers in the horticulture industry are aware of the great appeal of vivid contrasting colors to its buying public.

Dwarf Stature: The hybridizer achieved the dwarf height (30″) of this canna hybrid by selecting the parent plant Ambrosia for its height (24″). The desired influorescence color (red-yellow) of the other parent, Circus Clown (40″), and in this particular cultivar did achieve both goals.

Compact Growth: Another goal was to achieve compact growth habit in a cultivar displaying the striking red and yellow influorescence of parent plant, Circus Clown. The achievement of this growth habit is primarily shown by two characteristics: The stem thickness to overall plant height ratio and the internode spacing.

For example, in Liberty® Bugle Boy, the stem thickness (1½″) to height (30″) ratio is 20 to 1. In the comparison plant, Circus Clown, the stem thickness (1″) to height (40″) ratio is 40 to 1. The internode spacing of Circus Clown is 8″ and the internode spacing of Liberty® Bugle Boy is 6″, creating a more dense, compact overall presentation.

This dwarf and very compact growth habit makes Liberty® Bugle Boy ideal for the smaller garden and landscape designs and the patio/pot culture trend.

High Multiplication Rate: For commercial production, plant increase (multiple rate) is very important. Liberty® Bugle Boy increases an average of 8 rhizomes in USDA zone 5 in one season (5 month period) and as high as 20 rhizomes in a USDA zone 9 within one year. This is contrasted with a multiplication rate of 5–12 in Ambrosia: 7–14 in Circus Clown; for the same growing conditions and time frame. Though there are a few cannas of either dwarf stature or adequate multiplication rate, or bi-color influorescence in today's market, applicant is not aware of any that meet all these criteria as completely as does Liberty® Bugle Boy.

Winter Storage: The storage capability of Liberty® Bugle Boy is another characteristic that renders this cultivar advantageous both to home gardeners and to commercial growers. The rhizomes are superior for storage because an average of 98% of stored rhizomes are viable after the winter storage period.

The winter storage capability of Liberty® Bugle Boy is very important for two reasons. Since cannas are only grown as perennials in USDA zones 9–10 and must be dug and stored in zones 3–8, a vast majority of home gardeners must routinely dig and store the rhizomes during the winter months. There is great variance as to the ability of different varieties to store successfully. Liberty® Bugle Boy survives winter storage with a high rate of success. Secondly, this storage ability of Liberty® Bugle Boy is of great advantage to commercial cannas growers in USDA zones where the cannas must be dug and stored over winter months and a high degree of plant loss renders the product of no marketable value.

Comparison to Known Varieties: The cultivar may be compared with known varieties along the following lines.

Only closely related cultivars (both parent plants) are appropriate for comparison to Liberty® Bugle Boy. The pod parent plant is "Ambrosia" and the pollen parent is known in commercial trade as "Circus Clown".

"Ambrosia"

Bugle Boy is similar to "Ambrosia" in its compact growth habit, green foliage, and thick (relative to overall size of the plant) stems and rhizomes. Ambrosia is dissimilar in that the influorescence is salmon pink, its average height only 67% as tall, and it does not store as well during winter months.

"Circus Clown"

"Circus Clown" is similar to Bugle Boy in the color of its influorescence; however, the orange portion of the bi-colored splashed bloom is a much lighter color. The overall size of the "Circus Clown" plant is 25% larger than Bugle Boy and "Circus Clown's" stalk and leaf structure is thinner and more open in form. The overall bloom display (influorescence), leaf size, and plant height are not as well balanced as in Bugle Boy.

I claim:

1. A new and distinct cultivar of Canna, substantially as described and illustrated herein, characterized particularly as to novelty by its dwarf height, with overall compact growth characteristics, a multiplication rate of six to twenty plants per growing season, an influorescence with a unique distribution of bright red-orange and yellow colors, and strong winter storage capability providing a cultivar well suited as a garden or pot plant having no unusual susceptibility to the traditional Canna diseases and insects.

* * * * *